US010852448B2

(12) United States Patent
Song et al.

(10) Patent No.: US 10,852,448 B2
(45) Date of Patent: Dec. 1, 2020

(54) DEAD PIXEL CORRECTION FOR DIGITAL PET RECONSTRUCTION

(71) Applicant: KONINKLIJKE PHILIPS N.V., Eindhoven (NL)

(72) Inventors: Xiyun Song, San Jose, CA (US); Chuanyong Bai, Solon, OH (US); Andriy Andreyev, Willoughby Hills, OH (US); Bin Zhang, Cleveland, OH (US); Shushen Lin, Cleveland, OH (US); Jinghan Ye, Livermore, CA (US); Michael Allen Miller, Cleveland Heights, OH (US); Zhiqiang Hu, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/469,605

(22) PCT Filed: Dec. 6, 2017

(86) PCT No.: PCT/EP2017/081599
§ 371 (c)(1),
(2) Date: Jun. 13, 2019

(87) PCT Pub. No.: WO2018/108641
PCT Pub. Date: Jun. 21, 2018

(65) Prior Publication Data
US 2019/0361136 A1 Nov. 28, 2019

Related U.S. Application Data

(60) Provisional application No. 62/433,941, filed on Dec. 14, 2016.

(51) Int. Cl.
*A61B 6/03* (2006.01)
*G01T 1/24* (2006.01)
(Continued)

(52) U.S. Cl.
CPC ............ *G01T 1/2985* (2013.01); *A61B 6/037* (2013.01); *A61B 6/4258* (2013.01); *G01T 1/249* (2013.01); *G01T 7/00* (2013.01); *G06T 5/005* (2013.01)

(58) Field of Classification Search
CPC ....... A61B 6/037; A61B 6/4258; G01T 1/249; G01T 1/2985; G01T 7/00; G06T 5/005
See application file for complete search history.

(56) References Cited

U.S. PATENT DOCUMENTS 6,694,172 B1  2/2004 Gagnon
2008/0226032 A1  9/2008 Li
(Continued)

FOREIGN PATENT DOCUMENTS

CN  104939859 A  9/2015
WO  2012066443 A1  5/2012
(Continued)

OTHER PUBLICATIONS

International Search Report/Written Opinion for PCT/EP2017/081599, dated Mar. 9, 2018.

*Primary Examiner* — Mark R Gaworecki

(57) ABSTRACT

A PET detector array (8) comprising detector pixels acquires PET detection counts along lines of response (LORs). The counts are reconstructed to generate a reconstructed PET image (36, 46). The reconstructing is corrected for missing LORs which are missing due to dead detector pixels of the PET detector array. The correction may be by estimating counts along the missing LORs (60) by interpolating counts along LORs (66) neighboring the missing LORs. The interpolation may be iterative to handle contiguous groups of missing detector pixels. The correction may be by computing a sensitivity matrix having matrix elements corresponding to image elements (80, 82) of the reconstructed PET image. In this case, each matrix element is computed as a (Continued)

summation over all LORs intersecting the corresponding image element excepting the missing LORs. The computed sensitivity matrix is used in the reconstructing.

15 Claims, 9 Drawing Sheets

(51) Int. Cl.
*G01T 7/00* (2006.01)
*G06T 5/00* (2006.01)
*G01T 1/29* (2006.01)
*A61B 6/00* (2006.01)

(56) References Cited

U.S. PATENT DOCUMENTS

| | | |
|---|---|---|
| 2011/0235940 A1 | 9/2011 | Pavkovich |
| 2016/0015351 A1 | 1/2016 | Konno |

FOREIGN PATENT DOCUMENTS

| | | | | |
|---|---|---|---|---|
| WO | 2015145301 A1 | 10/2015 | | |
| WO | WO-2015145301 A1 * | 10/2015 | ............... | G01T 7/00 |
| WO | 2016103090 A1 | 6/2016 | | |

* cited by examiner

DEAD PIXEL CORRECTION FOR DIGITAL PET RECONSTRUCTION

CROSS-REFERENCE TO PRIOR APPLICATIONS

This application is the U.S. National Phase application under 35 U.S.C. § 371 of International Application No. PCT/EP2017/081599, filed on Dec. 6, 2017, which claims the benefit of U.S. Provisional Patent Application No. 62/433,941, filed on Dec. 14, 2016. These applications are hereby incorporated by reference herein.

FIELD

The following relates generally to the medical imaging arts, positron emission tomography (PET) imaging arts, radiation detector arts, and related arts.

BACKGROUND

In PET imaging, a radiopharmaceutical is administered to a patient (or other imaging subject, e.g. a veterinary subject). The radiopharmaceutical is designed to collect in an organ or tissue of interest. In some functional studies, the radiopharmaceutical is designed to flow through the organ or tissue of interest, e.g. intravascularly administered radiopharmaceutical may flow with the blood supply into and out of the brain. The radiopharmaceutical emits positrons, and each consequent electron-positron annihilation event emits two oppositely directed 511 keV gamma rays. Using a PET detector array, usually arranged as a ring, these oppositely directed 511 keV gamma rays are detected by two detector pixels, and the source positron is thus known to lie upon a line of response (LOR) connecting the two detector pixels. The gamma rays travel at the speed of light: in conventional PET the two 511 keV gamma ray detection events are simultaneous within the temporal resolution of the detector pixels. In time-of-flight (TOF) PET, the detector pixels have sufficient temporal resolution to detect a time difference (or lack thereof) between the two 511 keV gamma ray detection events and thereby provide TOF localization along the LOR with spatial resolution commensurate with the temporal resolution.

The PET detector array is a costly component, and is usually manufactured as modules with each module including a certain number of detector pixels. The detector pixels are precision photonic devices, and can occasionally fail. If one or only a few detector pixels of a module malfunction, then it is not cost-effective to replace the entire module. These malfunctioning, i.e. "dead", detector pixels usually produce no data, and the impact of a small number of dead detector pixels on the quality of the resulting reconstructed PET image is usually assumed to be negligible. If the number of dead detector pixels in a single module becomes too high, then the module may be replaced so as to correct the problem.

The following discloses a new and improved systems and methods that address the above referenced issues, and others.

SUMMARY

In one disclosed aspect, a positron emission tomography (PET) imaging device is disclosed, including a PET detector array comprising detector pixels configured to acquire counts of oppositely directed 511 keV gamma ray pairs along lines of response (LORs). The PET imaging device further includes a computer and a non-transitory storage medium storing instructions readable and executable by the computer to perform operations including reconstructing the counts along the LORs to generate a reconstructed PET image, and correcting the reconstructing for missing LORs which are missing due to dead detector pixels of the PET detector array. In some embodiments, the correction comprises estimating counts along the missing LORs by interpolating counts along available LORs neighboring the missing LORs. In some embodiments the correction comprises computing a sensitivity matrix having matrix elements corresponding to image elements of the reconstructed PET image, in which each matrix element is computed as a summation over all LORs intersecting the corresponding image element excepting the missing LORs. The computed sensitivity matrix is used in the reconstructing.

In another disclosed aspect, a non-transitory storage medium is disclosed, which stores an index of dead detector pixels which identifies dead detector pixels of a PET detector array. The non-transitory storage medium further stores instructions readable and executable by a computer to generate a reconstructed PET image from counts acquired using the PET detector array of oppositely directed 511 keV gamma ray pairs along LORs by operations including: computing a sensitivity matrix having matrix elements corresponding to image elements of the reconstructed PET image wherein each matrix element is computed as a summation over all LORs intersecting the corresponding image element excepting missing LORs which are missing due to dead detector pixels indexed in the index of dead detector pixels; and performing iterative image reconstruction of the counts acquired using the PET detector array to generate the reconstructed PET image wherein the iterative image reconstruction includes normalizing intensities of image elements of the reconstructed PET image using the corresponding matrix elements of the sensitivity matrix.

In another disclosed aspect, a PET image reconstruction method is disclosed, which operates on counts acquired by a PET detector array of oppositely directed 511 keV gamma ray pairs along LORs. The PET image reconstruction method comprises: estimating counts along missing LORs which are missing due to dead detector pixels of the PET detector array by interpolating counts along LORs neighboring the missing LORs; and reconstructing into a reconstructed PET image an image data set including both the counts acquired by the PET detector array of oppositely directed 511 keV gamma ray pairs along the LORs and the estimated counts along the missing LORs. The estimating of counts along the missing LORs may comprise: performing a first interpolation pass in which counts along the missing LORs having at least a minimum number of neighboring LORs that are not missing are interpolated using only counts along LORs that are not missing; and performing at least one additional interpolation pass in which counts along the missing LORs having less than the minimum number of neighboring LORs that are not missing are interpolated using both counts along LORs that are not missing and/or interpolated counts from a previous interpolation pass.

One advantage resides in providing improved image quality and quantitative accuracy in reconstructed PET images.

Another advantage resides in providing improved image quality of PET sinogram images.

Another advantage resides in providing improved image quality and quantitative accuracy in PET images reconstructed from sinograms (with or without time-of-flight binning).

Another advantage resides in providing improved image quality and quantitative accuracy in diagnostic PET images reconstructed from list mode data (with or without time-of-flight localization).

Another advantage resides in providing improved image quality and quantitative accuracy in reconstructed PET images by way of accurate interpolation of counts for missing lines of response (LORs) which are missing due to dead detector pixels.

Another advantage resides in providing improved image quality and quantitative accuracy in reconstructed PET images by way of improved normalization of intensities of image elements of the reconstructed PET image using a more accurate sensitivity matrix.

Another advantage resides in providing extended operating lifetime for PET detector array modules by facilitating continued use of detector modules with higher numbers of dead pixels.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
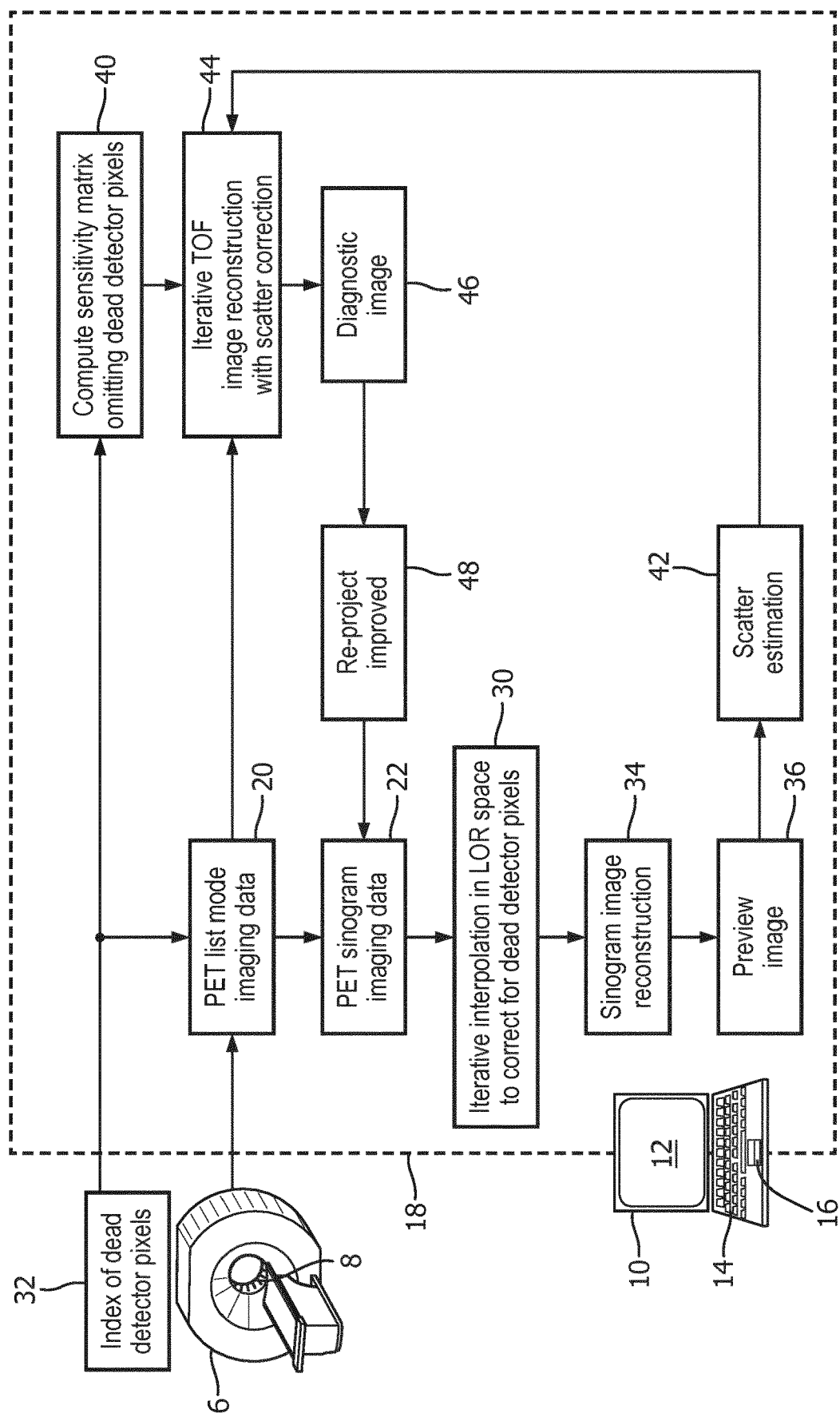
FIG. 1 diagrammatically shows an illustrative positron emission tomography (PET) imaging device including correction for dead detector pixels.

Embodiments disclosed herein are founded in part in the recognition that in some circumstances the impact of even a small number of dead detector pixels on reconstructed PET image quality may be significant. Each dead (such that receives either no signal or abnormal signal, thus also declared as dead) detector pixel results in dozens or even hundreds of missing lines of response (LORs). In sinogram-based reconstruction techniques, a single dead pixel introduces entire lines of missing sinogram data. In some embodiments, this is addressed by estimating counts along the missing LORs by interpolating counts along LORs neighboring the missing LORs. The interpolation is in "LOR-space" rather than at the detector level.

It is further recognized herein that such interpolation may be hindered in the case of contiguous groups of dead pixels, since in this case there may be no available neighboring LORs to provide the counts for interpolation. To address such situations, it is further disclosed to employ iterative interpolation, working inward from the edges of the contiguous group of missing detector pixels. In one such iterative approach, a first interpolation pass is performed in which counts along the missing LORs having at least a minimum number of neighboring LORs that are not missing are interpolated using only counts along LORs that are not missing. At least one additional interpolation pass (or as many as needed) is thereafter performed, in which counts along the missing LORs having less than the minimum number of neighboring LORs that are not missing are interpolated using both counts along LORs that are not missing and/or interpolated counts from a previous interpolation pass.

Other embodiments disclosed herein address the impact of dead detector pixels in the case of iterative reconstruction of list mode data. In this case the missing LORs have zero counts, and thus it might seem that the missing LORs would merely amount to a slightly reduced quantity of list mode data with little impact on image quality. However, it is recognized herein that the missing LORs have detrimental impact by imposing inconsistency on the sensitivity matrix that is sometimes used in normalizing intensities of image elements of the reconstructed PET image. The sensitivity matrix is typically computed from the detector array geometry (all possible LORs), rather than the actually collected counts. Failure to account for the impact of dead detector pixels on the sensitivity matrix can degrade image quality and quantitative accuracy. In embodiments disclosed herein, the matrix elements of the sensitivity matrix (which correspond to image elements of the reconstructed PET image) are computed as summations over all LORs intersecting the corresponding image elements, excepting missing LORs which are missing due to dead detector pixels. In other words, the summation used in computing a sensitivity matrix element omits any LORs that are missing due to a dead detector pixel to ensure the consistency between the sensitivity matrix and acquired data.

With reference to FIG. 1, an illustrative imaging device comprises a positron emission tomography (PET) imaging device (or scanner) 6 that includes a PET detector array 8, and an electronic processor 10 programmed to process imaging data acquired by the PET imaging scanner 6 to generate one or more reconstructed PET images. Processing performed by the electronic processor 10 is diagrammatically indicated in FIG. 1 by way of a dashed box 18 enclosing blocks graphically representing data and operations of the processing flow. The PET detector array 8 acquires counts of oppositely directed 511 keV gamma ray pairs along lines of response (LORs). The counts may or may not include time of flight (TOF) localization. The counts along each LOR are acquired by two detector pixels of the detector array 8 that are intersected by the LOR. By way of some non-limiting illustrative examples, the illustrative PET imaging scanner 6 may be the PET gantry of a Vereos™ Digital PET/CT scanner, available from Koninklijke Philips N.V., Eindhoven, the Netherlands. It may be noted that while the PET detector array 8 is shown as a detector array ring which is visible on the inside circumference of the bore of the PET scanner 6, this is for illustrative purposes and more typically the PET detector array is occluded from view by a cosmetic bore liner or the like which passes 511 keV radiation.

The electronic processor 10 may, for example, be embodied as a computer 10 (e.g. a desktop computer, network-based server computer, a dedicated PET control computer, various combinations thereof, or so forth) that executes instructions read from one or more non-transitory storage media (e.g. one or more hard drives, optical disks, solid state drives or other electronic digital storage devices, various combinations thereof, or so forth) that stores the instructions. The computer 10 typically includes or has operative access to at least one display 12 (e.g. an LCD display, plasma display, or so forth), and may also optionally include or have operative access to at least one user input device via which a user can input information. The illustrative user input devices include a keyboard 14 and a trackpad 16; some other typical user input devices include a mouse, a touch-sensitive overlay of the display 12, and/or so forth.

In the illustrative embodiment of FIG. 1, the PET scanner 6 acquires counts along LORs formatted as list mode imaging data 20, in which each count is stored individually along with its time stamp (and optional TOF localization). The list mode data 20 can be converted to sinogram data 22 of the form (p, θ) where θ is the viewing angle (i.e. the angle of the LOR) and p is a lateral offset, usually although not necessarily designated measured respective to the isocenter of the PET scanner 6. In other contemplated embodiments, the acquired counts are directly stored as sinogram data, without storing list mode data. The sinogram data 22 may be limited to two-dimensional slices, i.e. only LORs extending between two detector pixels of a same ring of detectors are included in the sinogram data 22. As previously noted, any missing detector pixels of the PET detector array 8 will result in lines of missing data in the sinograms. To correct for this, interpolation is performed in "LOR space" in an operation 30, to be described in greater detail later herein. Briefly, the interpolation 30 estimates counts along the missing LORs (missing due to dead detector pixels which prevent acquiring counts along those missing LORs) by interpolating counts along LORs neighboring the missing LORs. However, if there is a contiguous group of dead detector pixels, then missing LORs due to dead pixels in the interior of the group may have no neighboring LORs. To address this situation, the interpolation may be performed iteratively, working inward from the edges of the group.

As used herein, the term "dead detector pixel" refers to any detector pixel (typically known as small individual detector element) that is indexed as a dead detector pixel in an index of dead detector pixels 32. In other words, the dead detector pixels of the PET detector array 8 are defined as the set of detector pixels which are indexed in the index of dead detector pixels 32. Usually, a dead pixel is one that does not detect gamma rays, and such dead detector pixels may be identified using a standard calibration procedure, e.g. flood map estimation. However, it is contemplated for a detector pixel to be designated as a dead detector pixel by being included in the index 32 due to other malfunction besides lack of any output. For example, a detector pixel may be designated as a dead detector pixel by being included in the index 32 due to its having an unacceptably high noise level, or due to its producing frequent spurious data, or so forth. Such a detector pixel is referred to herein as a dead detector pixel even though it may produce some output any output from any dead detector pixel is ignored or discarded.

In the illustrative workflow, a sinogram data set including the sinogram data 22 combined with interpolated counts for the missing LORs generated in the operation 30 is reconstructed using a sinogram image reconstruction 34. As the imaging data is in a sinogram format, the reconstruction 34 may be executed by performing line integrals, e.g. an inverse Radon transform, on at least one sinogram generated from the combination of the counts 22 along the LORs and the estimated counts along the missing LORs from operation 30. In a common approach, the detector array 8 includes a set of detector rings spaced apart along an axial direction (i.e. the direction of the axis of the bore of the PET scanner 6), and each detector ring acquires a two-dimensional (2D) sinogram that is reconstructed to generate an image slice using an inverse Radon transform or other line integral. The resulting stack of 2D slices may optionally be treated as a three-dimensional (3D) reconstructed image. This type of image reconstruction is fast, but loses information as counts for LORs that are detected by different detector rings are not used (or alternatively are assigned to neighboring 2D sinograms, in the process losing the spatial information precision, or employing sinograms with an angular sampling or tilt dimension, again losing some information), and moreover correction such as scatter correction may be omitted. Thus, the reconstructed PET image produced by the fast sinogram reconstruction 34 is commonly used as a preview image 36.

In an additional or alternative image reconstruction path, the PET list mode or sinogram imaging data 20 may be reconstructed using an iterative reconstruction 44 operating in 3D and optionally including various correction(s) such as scatter correction. An illustrative formulation of the iterative reconstruction 44 is as follows:

$$f_i^{(n+1)} = \frac{f_i^{(n)}}{s_i} \sum_j H_{ij} \frac{g_j}{\Sigma_i H_{ij} f_i^{(n)} + Corr_j} \quad (1)$$

where $f_i^{(n)}$ is the current estimate of the activity in voxel i, $H_{ij}$ is the probability that an electron-positron annihilation initiated at voxel i is detected at LOR j or a projection bin j as a coincidence event, $g_j$ denotes counts detected along LOR j or projection bin j, and the superscripts (n) and (n+1) denote the last and current iterations of the iterative reconstruction 44, respectively. $Corr_j$ are various optional corrections (e.g. scatter and/or randoms) factors, which can be either pre-computed or computed on-the-fly based on the previous update of $f^{(n)}$. The factor $S_i$ is the matrix element of the sensitivity matrix corresponding to image element i. Equation (1) is applied for all image elements of the image volume to update the image elements from $f_i^{(n)}$ to $f_i^{(n+1)}$, and this is repeated iteratively. It is to be understood that Equation (1) is an illustrative general form, and that the iterative image reconstruction 44 may implement various specific iterative image reconstruction algorithms, e.g. maximum likelihood-expectation maximization (MLEM) image reconstruction, ordered subset expectation maximization (OSEM), or so forth. The iterative image reconstruction may optionally utilize time-of-flight (TOF) localization information, typically embodied in the detection probability $H_{ij}$ and/or the count information $g_j$ depending upon the iterative TOF image reconstruction formulation.

The sensitivity matrix having matrix elements $S_i$ is computed from the geometry of the detector array 8, and accounts for the fact that different image elements $f_i$ in general have different numbers of LOR intersections. If this is not accounted for, then those image elements that have more intersecting LORs will have artificially higher intensities as compared with those image elements with fewer intersecting LORs. The sensitivity matrix elements $S_i$ of Equation (1) normalize the intensities of the image elements of the reconstructed PET image to correct for this. However, it is recognized herein that the computation of the sensitivity matrix should take into account any missing LORs due to dead detector pixels. This is because a missing LOR contributes nothing to the intensities of the image elements that it intersects, because the missing LOR has no counts. To account for this, in the illustrative embodiment of FIG. 1 an operation 40 computes each matrix element $S_i$ as a summation over all LORs intersecting the corresponding image element i excepting the missing LORs (if any) which are missing due to dead detector pixels indexed in the index of dead detector pixels 32. In other words, the missing LORs are not included in the summation over all LORs used to compute matrix element $S_i$. In an illustrative example, using the same notation as is employed in Equation (1):

$$S_i \propto \sum_{j \in \mathcal{D}} H_{ij} \cdot 1 \qquad (2)$$

where, in addition to the notation already defined with reference to Equation (1), $\mathcal{D}$ is the set of all LORs intersecting the image element i excepting the missing LORs. The missing LORs which are not included in the set $\mathcal{D}$ are any LORs that intersect the image element indexed by i and that also intersect (and hence would have counts acquired using) one of the dead detector pixels indexed in the index of dead detector pixels 32. Due to the dead detector pixel the counts for that missing LOR are not actually acquired, and this is properly reflected in the sensitivity matrix element $S_i$ by summing over the set $\mathcal{D}$ which omits those missing LORs (if any). Note that should the data be interpolated, i.e. filling in for the missing LORs as in the operation 30, then all missing LORs are considered "available" and the estimation of the sensitivity matrix $S_i$ should still be done over all possible LORs (including physically dead or missing ones). More generally, back-projection in calculation of sensitivity matrix should always match the back-projection in iterative reconstruction.

With returning reference to Equation (1), as previously noted the term $Corr_j$ represents various optional corrections, e.g. scatter and/or randoms. In the illustrative example of FIG. 1, scatter estimation is suitably performed in an operation 42 using the preview image 36, e.g. regions of higher density in the preview image may be estimated to have higher scatter. Alternatively, scatter may be estimated using a computed tomography (CT), magnetic resonance (MR), or other image providing anatomical information.

The iterative image reconstruction 44 performed natively in 3D and employing all data (e.g., not omitting LORs between detector pixels on different detector rings) is expected to produce an image having higher image quality as compared with the preview image 36. Accordingly, the output of the iterative image reconstruction 44 is sometimes used as a diagnostic image 46, e.g. this is the image supplied to a doctor or other medical professional to perform medical diagnosis, medical treatment assessment, or other clinical tasks. In some instances, such as when the preview image 36 is used in operation 42 to provide a scatter estimation, there may be value in improving the quality of the preview image 36. To this end, in some embodiments, the diagnostic image 46 is re-projected in an operation 48 to produce an improved sinogram that can replace the original sinogram data 22 and may be reconstructed as per operation 34 to provide an improved preview image. (In this second pass, the iterative interpolation 30 is suitably omitted).

Having provided an overview of illustrative PET image reconstruction processing including dead detector pixel correction with reference to the illustrative PET imaging device diagrammatically shown in FIG. 1, in the following the operations 30, 40 which provide dead pixel correction are described in further detail.

Figure 2:
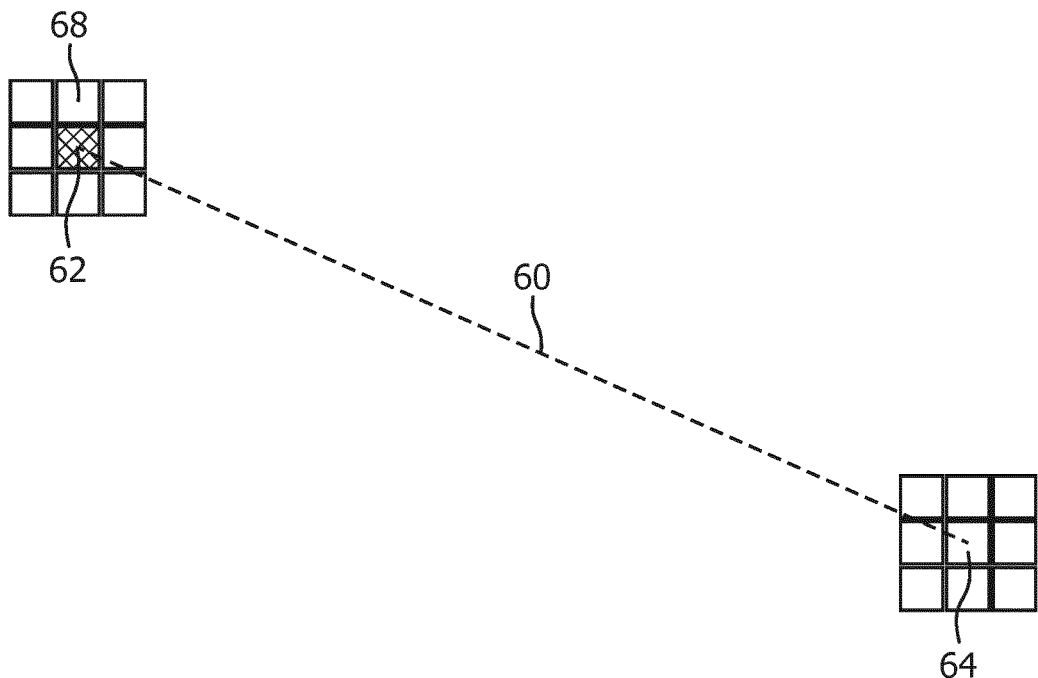
FIGS. 2-7 diagrammatically illustrate aspects of dead detector pixel correction techniques described herein.

With reference to FIGS. 2-6, estimation of the counts along a missing LOR 60 by interpolating counts along LORs neighboring the missing LOR 60 (that is, operation 30 of FIG. 1) is diagrammatically shown. As shown in FIG. 2, the LOR 60 intersects a detector pixel 62 on one detector module and a detector pixel 64 on another detector module. Thus, any counts of oppositely directed 511 keV gamma photons along the LOR 60 would be detected by the two detector pixels 62, 64. However, the detector pixel 62 is a dead detector pixel, as diagrammatically indicated in FIG. 2 using shading. The dead detector pixel 62 is dead because it is listed as a dead pixel in the index 32 of FIG. 1. As previously noted, this may be because the dead detector pixel 62 actually provides no output due to some malfunction, or it may be because the dead detector pixel 62 was designated as a dead detector pixel in the index 32 for some other reason, e.g. excessive noise, production of spurious signals, inaccurate time stamping, or so forth. Due to the dead detector pixel 62, the LOR 60 is a missing LOR—it is missing because there are no counts acquired along this LOR since the dead detector pixel 62 does not output any 511 keV gamma ray detections (or, if such detections are output, they are discarded since the detector pixel 62 is listed as a dead detector pixel in the index 32).

Figure 3:
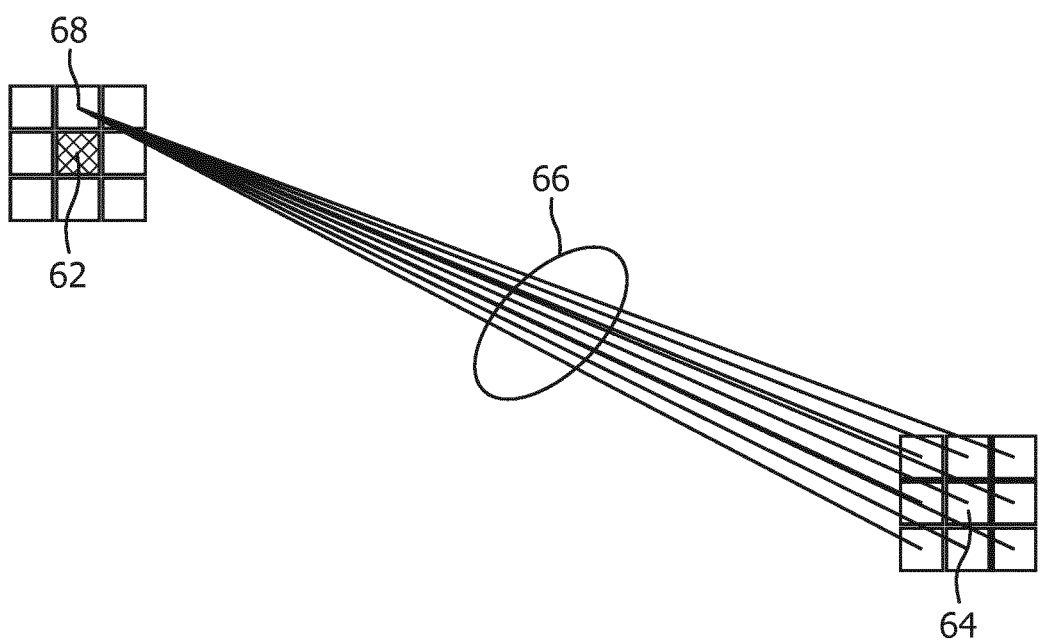

Turning now to FIG. 3, the interpolation of counts along LORs 66 neighboring the missing LOR 60 is diagrammatically shown. As seen in FIG. 3, there are nine neighboring LORs 66 provided by the labeled detector pixel 68 which is adjacent the dead detector pixel 62 in the detector module. The labeled detector pixel 68 is one of eight detector pixels that are immediately adjacent the dead detector pixel 62—another nine neighboring LORs (not shown in FIG. 3) are provided by each of the other seven detector pixels (not counting pixel 68) that also neighbor the dead detector pixel 62. Thus, by interpolating the counts along all LORs acquired by two detector pixels each of which is either one of the two detector pixels intersected by the missing LOR (only one of these is not dead, namely the detector pixel 64) or immediately adjacent one of the two detector pixels intersected by the missing LOR, the total number of neighboring LORs is 8×9=72 LORs. This is a large set of neighboring LORs from which to generate an accurate interpolation of the counts for the missing LOR 60 shown in FIG. 2.

In a variant situation, it could be that both detector pixels 62, 64 that intersect the missing LOR 60 are dead detector pixels. In this case, the neighboring LOR of FIG. 3 which runs from detector pixel 68 to detector pixel 64 will also be a missing LOR; more generally, any LOR running from any detector pixel neighboring the missing detector pixel 62 to detector pixel 64 will also be a missing LOR. In this case the total number of neighboring (operational) LORs is reduced to 8×8=64 LORs.

Figure 4:
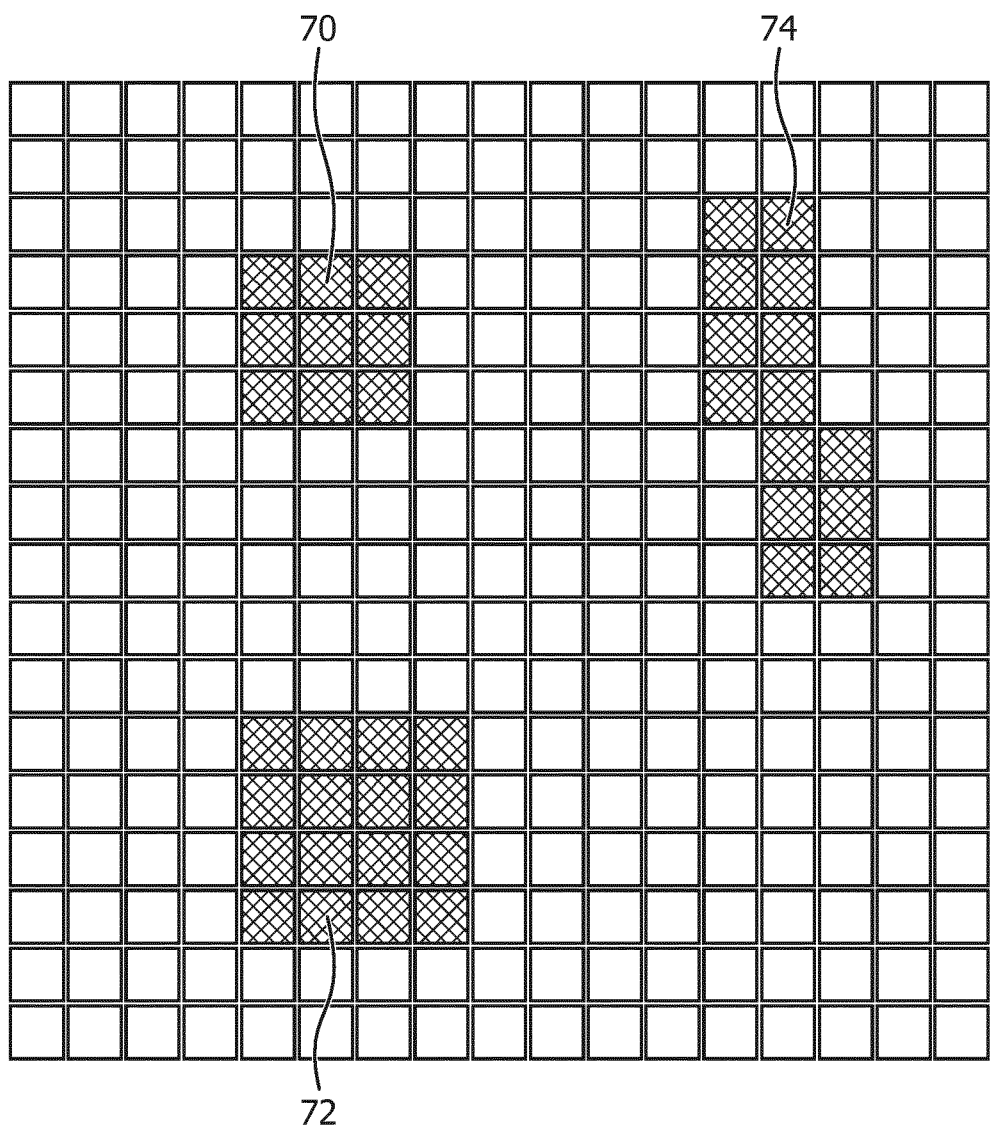
Figure 5:
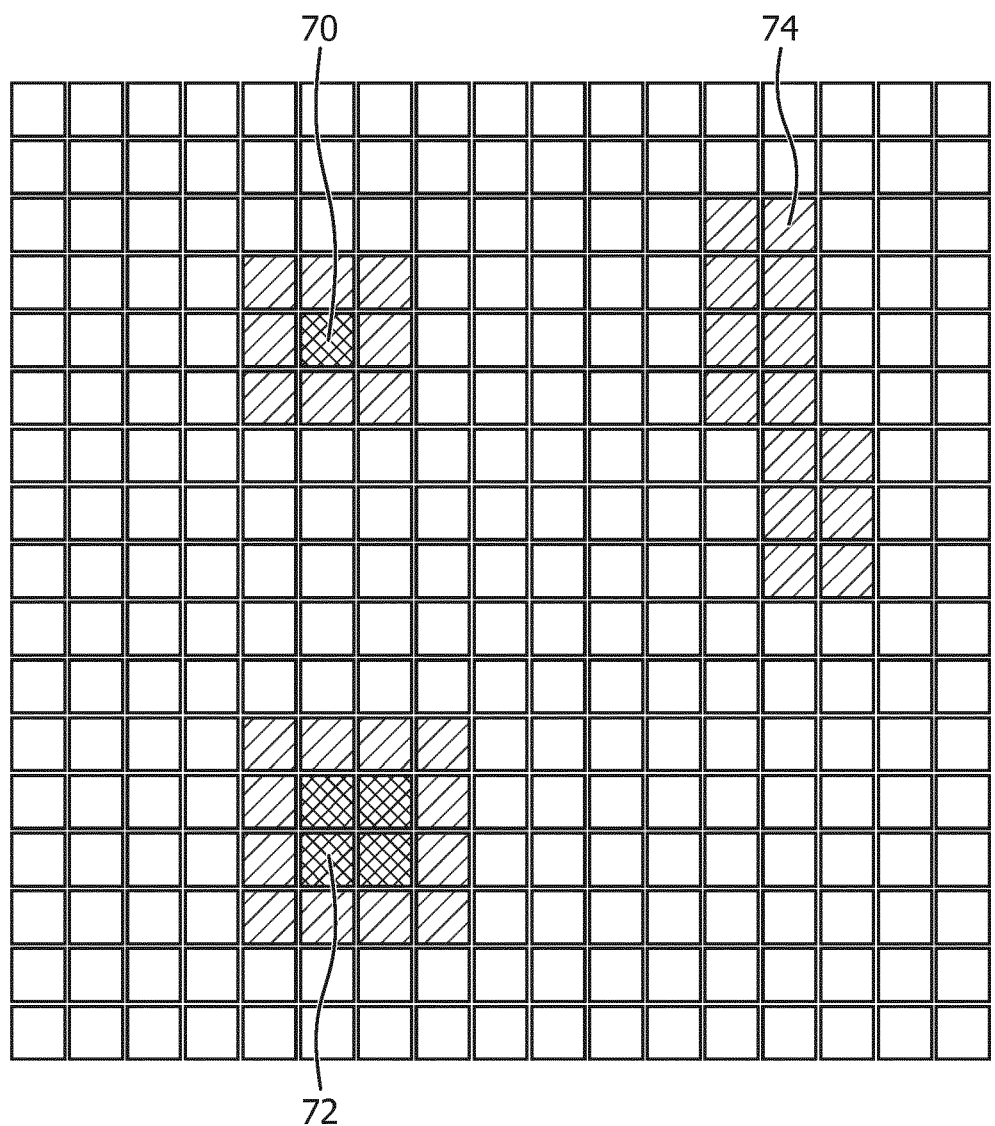
Figure 6:
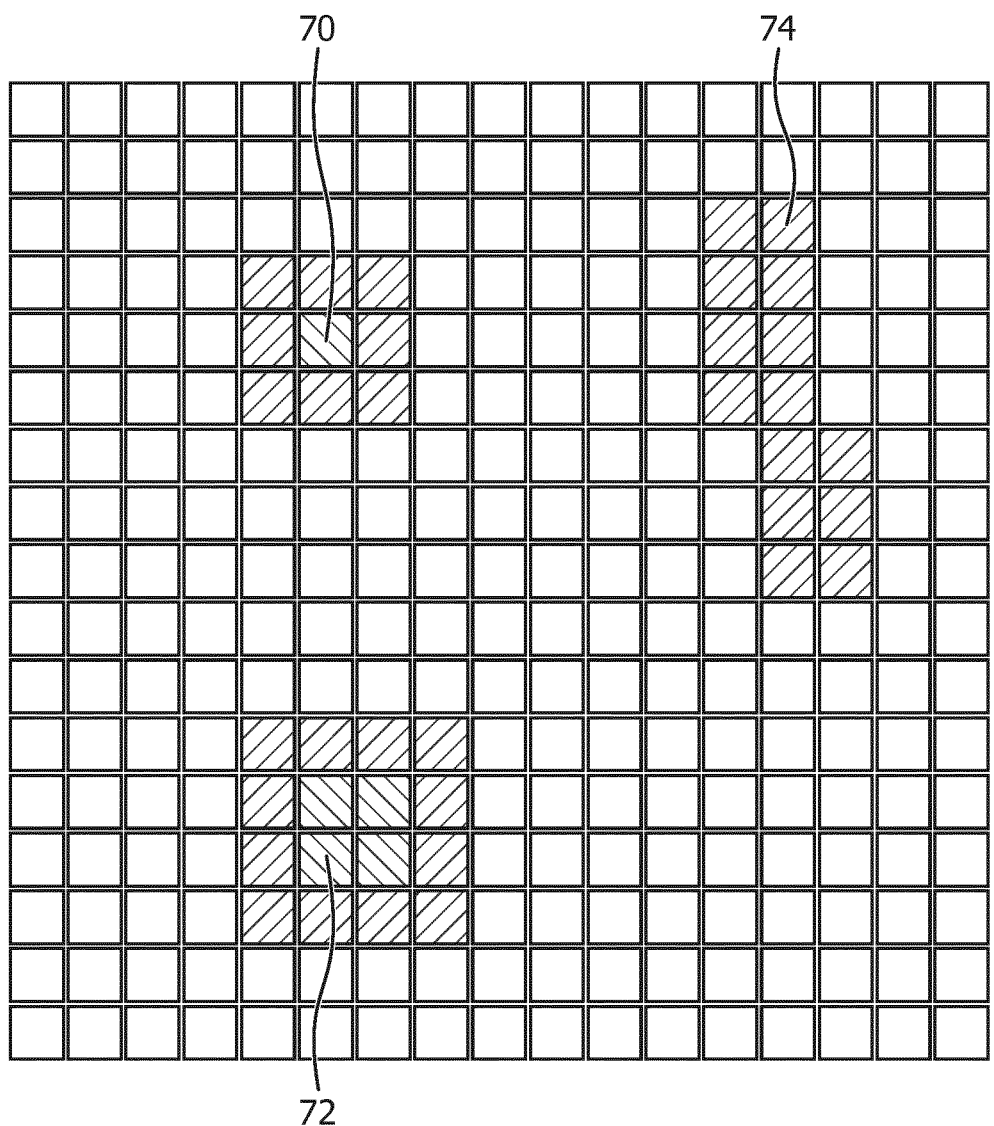

With reference now to FIGS. 4-6, the neighboring LOR interpolation approach of FIGS. 2 and 3 is extended to the situation in which some dead detector pixels are present in contiguous groups. Referring back to FIGS. 2 and 3, it is seen that the isolated dead detector pixel 62 has eight operational neighboring detector pixels on the same module. This is not the case if the dead detector pixel is part of a contiguous group of dead detector pixels, since one or more of its adjacent neighbors is also a dead detector pixel. Indeed, interior dead detector pixels of the contiguous group may have no operational neighboring detector pixels at all. To illustrate, FIG. 4 shows three contiguous groups of dead pixels 70, 72, 74 (where again dead detector pixels are indicated by shading). The dead detector pixel group 70 is a rectangular 3×3 array of dead detector pixels, so that the centermost dead detector pixel has no operational neighboring detector pixels. The dead detector pixel group 70 is a rectangular 4×4 array of dead detector pixels, so that the centermost 2×2 sub-array of dead detector pixels have no operational neighboring detector pixels. The dead detector pixel group 74 is an irregularly shaped group, which has fourteen dead detector pixels but none of which have no operational neighboring detector pixels.

Turning now to FIGS. 5 and 6, the iterative approach for interpolating counts for the dead detector pixels is described. FIG. 5 illustrates the result after a first interpolation pass in which counts along the missing LORs having at least a minimum number of neighboring LORs that are not missing (namely at least one neighboring LOR that is not missing in this example) are interpolated using only counts along LORs that are not missing. It will be recognized that those missing LORs that intersect a dead detector pixel with at least one operational neighboring detector pixel will have at least one neighboring LOR that is not missing (because that LOR is acquired using the operational neighboring detector pixel); whereas, this missing LORs that intersect a dead detector pixel with no operational neighboring detector pixels will have no neighboring LOR that is not missing. Thus, the LORs that intersect the group "edge" dead detector pixels shown in FIG. 5 by lighter shading now have estimated counts from interpolation; whereas, the LORs that intersect dead detector pixels that are shown in FIG. 5 with the same original (darker) shading of FIG. 4 are not (yet) estimated because they have no neighboring LORs. As seen in FIG. 5, the dead detector pixels whose LORs remain to be estimated are the central dead detector pixel of group 70, and the central 2×2 group of dead detector pixels of group 72.

Turning now to FIG. 6, the process is repeated iteratively, so that in a next interpolation pass counts along the missing LORs having less than the minimum number of neighboring LORs that are not missing (that is, that had no neighboring LORs that are not missing in this illustrative example) are interpolated using both counts along LORs that are not missing and interpolated counts from a previous interpolation pass. This second pass enables estimation of counts for the central dead detector pixel of group 70, and the central 2×2 group of dead detector pixels of group 72, as indicated by now using the lighter shading for these detector pixels. In this example, there are no remaining missing LORs to be estimated, so the process stops. In embodiments with larger groups of contiguous dead detector pixels, a third, fourth, or even more iterations may be needed to work inward in order to estimate counts for all missing LORs.

In the example of FIGS. 4-6, counts along missing LORs were estimated if the missing LOR has at least one neighboring LOR that is not missing. More generally, in other embodiments such estimation may be performed if the missing LOR has a minimum of two (or three, or four, et cetera) neighboring LORs that are not missing.

The foregoing interpolation approaches for handling dead pixels can also be applied to sinogram data. For a sinogram bin, the value in the bin can be derived from some associated LORs:

$$c_j = \sum_{l \in L_j} w_{jl} g_l \quad (3)$$

where $g_l$ is counts collected in LOR l, $w_{jl}$ is the contribution of a count in LOR l to sinogram bin j, $L_j$ is a set of LORs that have contribution to sinogram bin j. If some LORs within $L_j$ are dead, then without changing Equation (3) the interpolated sinogram bin would have a lower value than normal due to the dead detector pixels. To compensate for the dead LORs, Equation (3) can be modified as:

$$c_j = \tau_j \sum_{l \in L'_j} w_{jl} g_l \quad (4)$$

for $$\tau_j = \frac{\Sigma_{l \in L_j} w_{jl}}{\Sigma_{l \in L'_j} w_{jl}} \quad (5)$$

where $L'_j$ is either the subset of $L_j$ in which dead LORs are removed, or a set that includes all the good LORs in $L_j$, or a set that include not only all the good LORs in $L_j$, but also some neighbor (good) LORs. The binning strategy of Equations (4) and (5) can be applied either on-the-fly during PET acquisition, where each incoming event that belongs to an LOR l contributes to sinogram bin j, or generated from LOR acquisition data post acquisition. Another alternative for dead pixel compensation for sinogram data is applying dead pixel compensation first in LOR data, and then generating the sinogram data using the dead-pixel-compensated LOR data.

Figure 7:
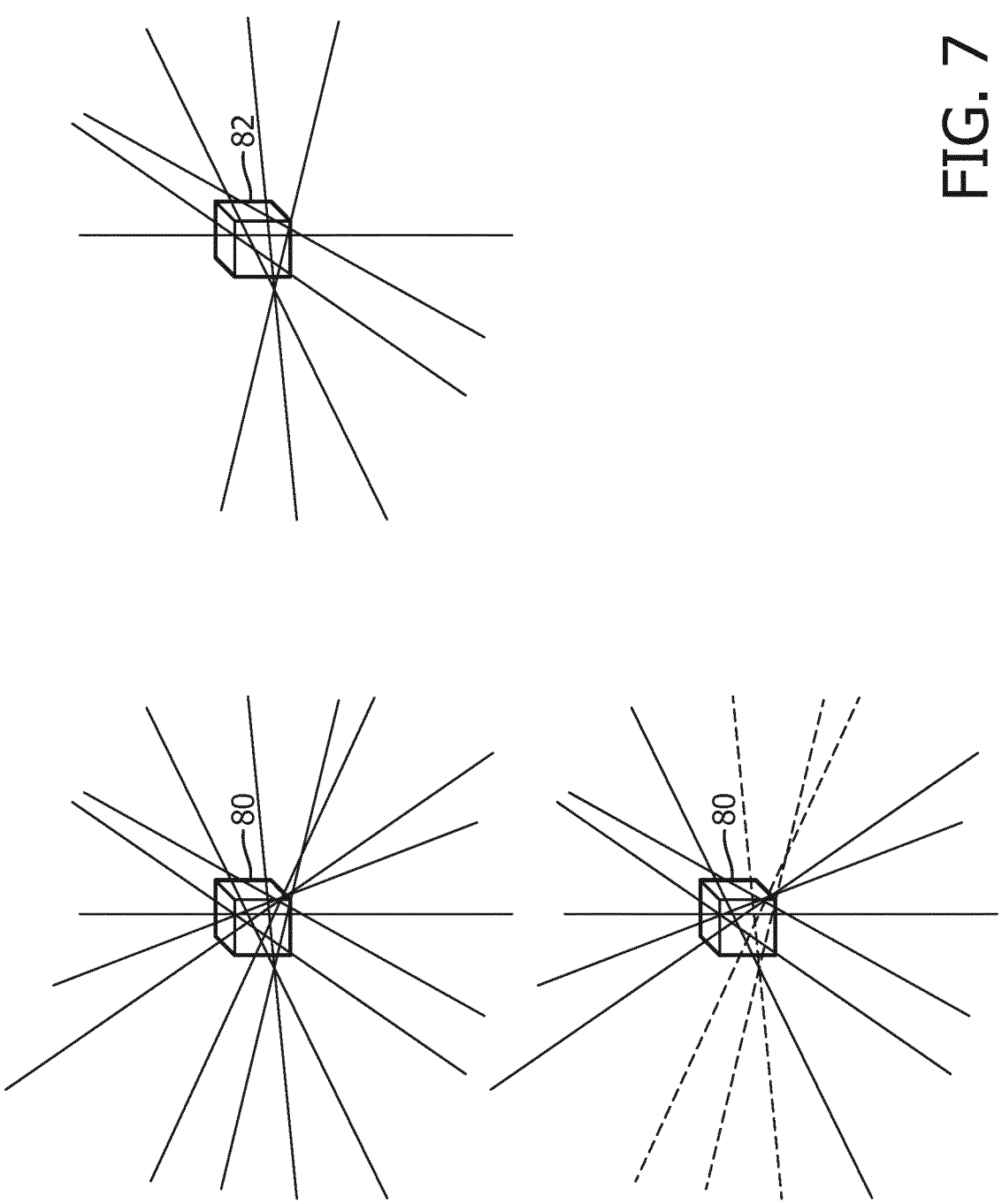

With reference now to FIG. 7, computing the sensitivity matrix elements as a summation over all LORs intersecting the corresponding image element excepting the missing LORs (that is, operation 40 of FIG. 1) is diagrammatically illustrated. The upper left diagram of FIG. 7 illustrates an image element 80 (e.g. voxel in 3D) which is intersected by nine LORs. The upper right diagram of FIG. 7 shows another illustrative image element 82 is intersected by six LORs. The reason for the different number of LORs intersecting the two image elements 80, 82 is in general due to the geometry of the PET detector array (e.g. ring) 8 (see FIG. 1)—for example, image element 80 may be closer to isocenter and hence in the field of view of more of the detector pixels, while image element 82 may be closer to an edge of the overall image field of view and hence in the field of view of fewer detector pixels. The reason for employing a sensitivity matrix for normalizing intensities of image elements of the reconstructed PET image can be illustrated by the following example. Suppose both image elements 80, 82 have the same amount of radiopharmaceutical. In this case, the two image elements 80, 82 should have the same reconstructed intensity. However, if the greater number of LORs passing through image element 80 versus image element 82 is not addressed, then image element 80 will be reconstructed with higher intensity than image element 82.

To correct for this, a sensitivity matrix element is computed according to $S_i \propto \Sigma_j H_{ij} \cdot 1$ where $H_{ij}$ is the contribution of a count along the LOR indexed j to intensity at the image element indexed i, and the summation is over all possible LORs intersecting the image element. In accord with this (and assuming $H_{ij} = h$ is a constant for simplicity), $S_i \propto 9h$ for image element 80 and $S_i \propto 6h$ for image element 82. When this normalization is applied during the iterative image reconstruction, e.g. according to Equation (1) presented previously herein, then differences in the number of LORs intersecting different image elements is corrected.

With reference now to the bottom left diagram of FIG. 7, the same image element 80 is shown, but now with three of the LORs being missing LORs, as indicated using dashed lines for these three missing LORs. Since the sensitivity matrix is computed based on the detector array geometry, these missing LORs do not change the calculation $S_i \propto \Sigma_j H_{ij} \cdot 1$ where the summation is over all LORs intersecting the image element. But as recognized herein, this result is inaccurate in the case shown in the bottom left diagram of FIG. 7, because it continues to weight image voxel 80 as if counts from the three missing LORs were being acquired. This is no longer the case due to those three LORs being missing LORs. The improved sensitivity matrix element of Equation (2) presented previously herein correctly accounts for this, by performing the summation only over the set D of all LORs intersecting the image element excepting the missing LORs. The sensitivity matrix element computed for image element 80 using Equation (2) in the case shown in the upper left diagram is $S_i \propto \Sigma_{j \in \mathcal{D}} H_{ij} \cdot 1 = 9h$, but in the case shown in the lower left diagram is $S_i \propto \Sigma_{j \in \mathcal{D}} H_{ij} \cdot 1 = 6h$, since the set $\mathcal{D}$ in the latter case omits the three missing LORs.

In the following, some simulation results are described.

Figure 8:
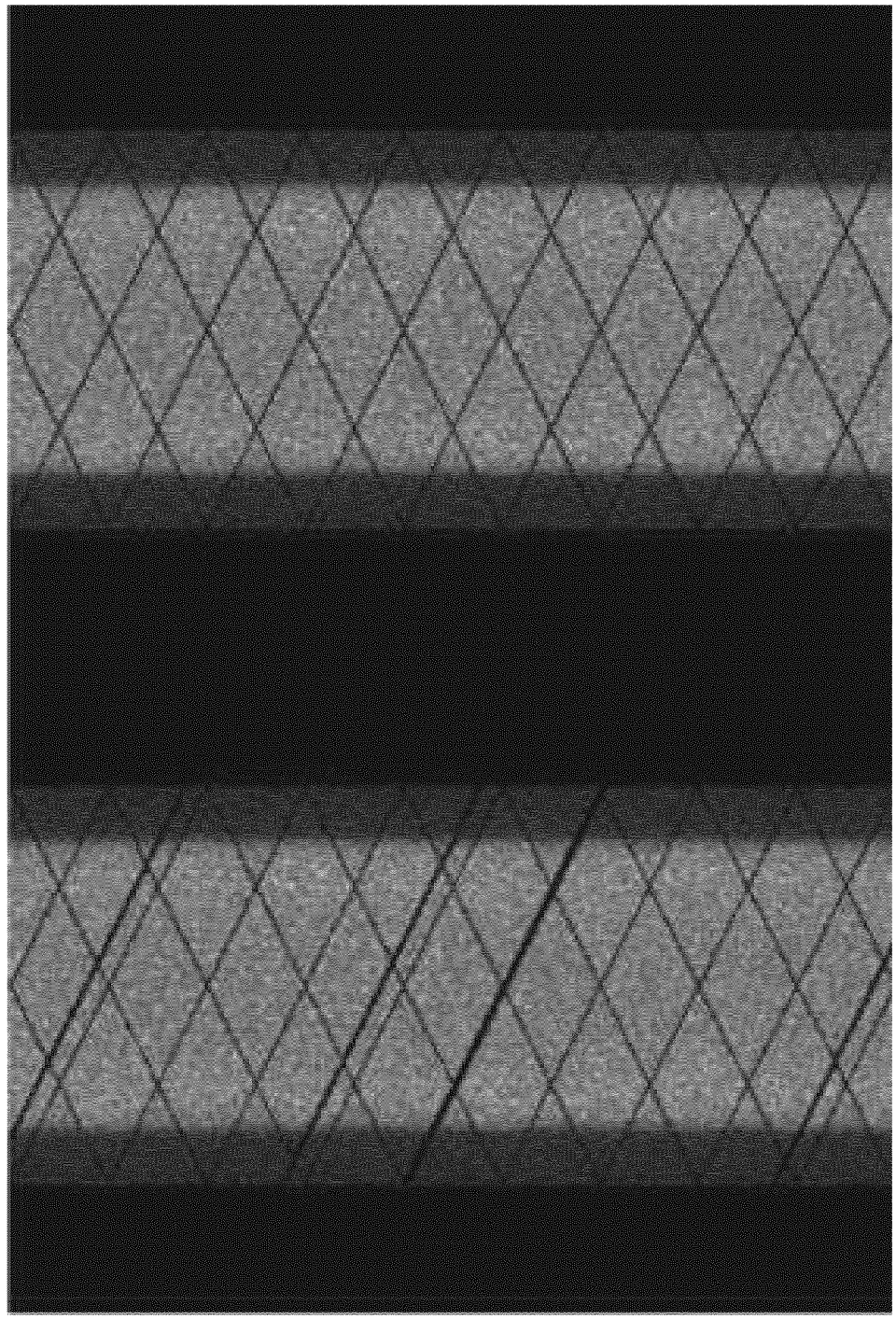
FIGS. 8-10 present simulation results as described herein.

With reference to FIG. 8, an example sinogram acquired from a uniform radioactivity-filled cylinder is shown without (left) and with (right) dead detector pixel handling in accordance with the iterative interpolation operation 30 of FIG. 1. Several dark streaks that are present in the sinogram on the left due to dead detector pixels are effectively removed from the sinogram on the right after applying the iterative interpolation in LOR space.

Figure 9:
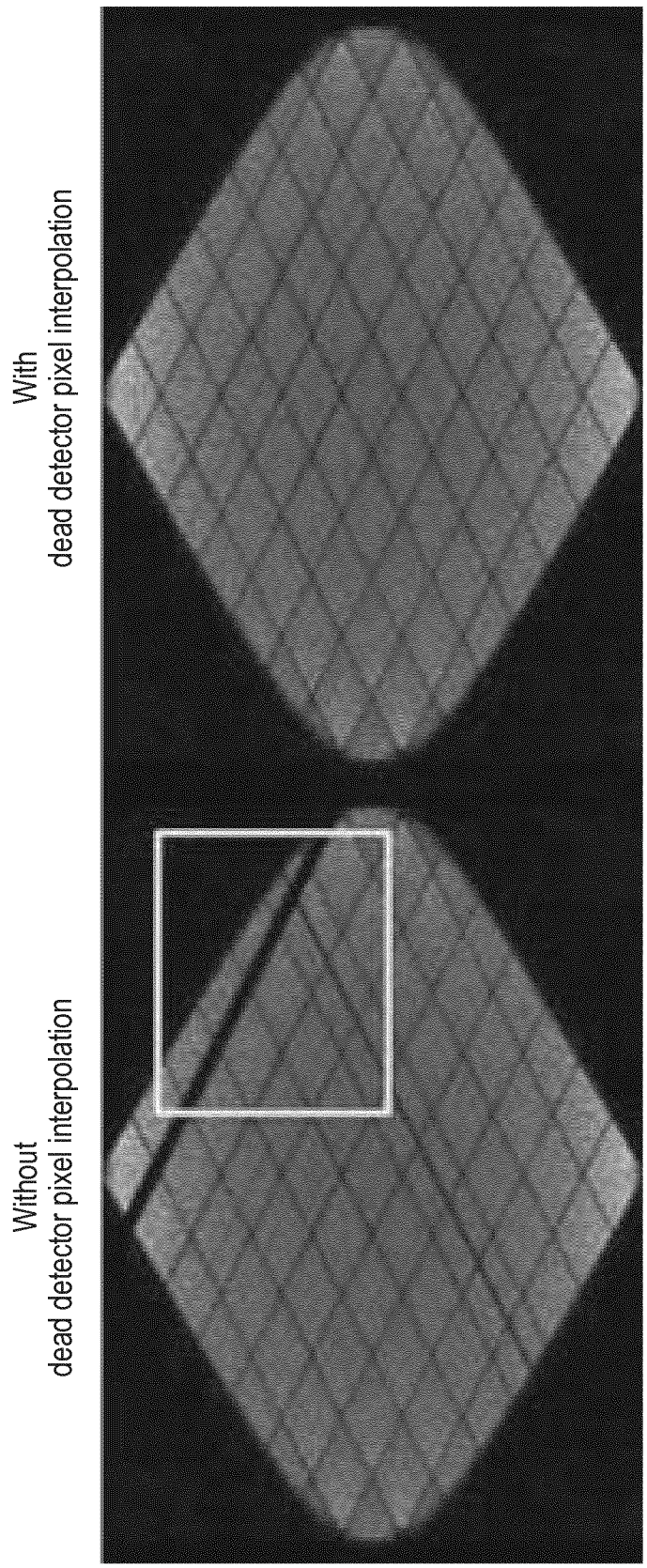

With reference to FIG. 9, sinograms from an image of a planar source are shown without (left) and with (right) dead detector pixel handling in accordance with the iterative interpolation operation 30 of FIG. 1. The wide dark strips that are present in the sinogram on the left due to contiguous groups of dead detector pixels (highlighted by a superimposed box) are effectively removed from the sinogram on the right after applying operation 30.

Figure 10:
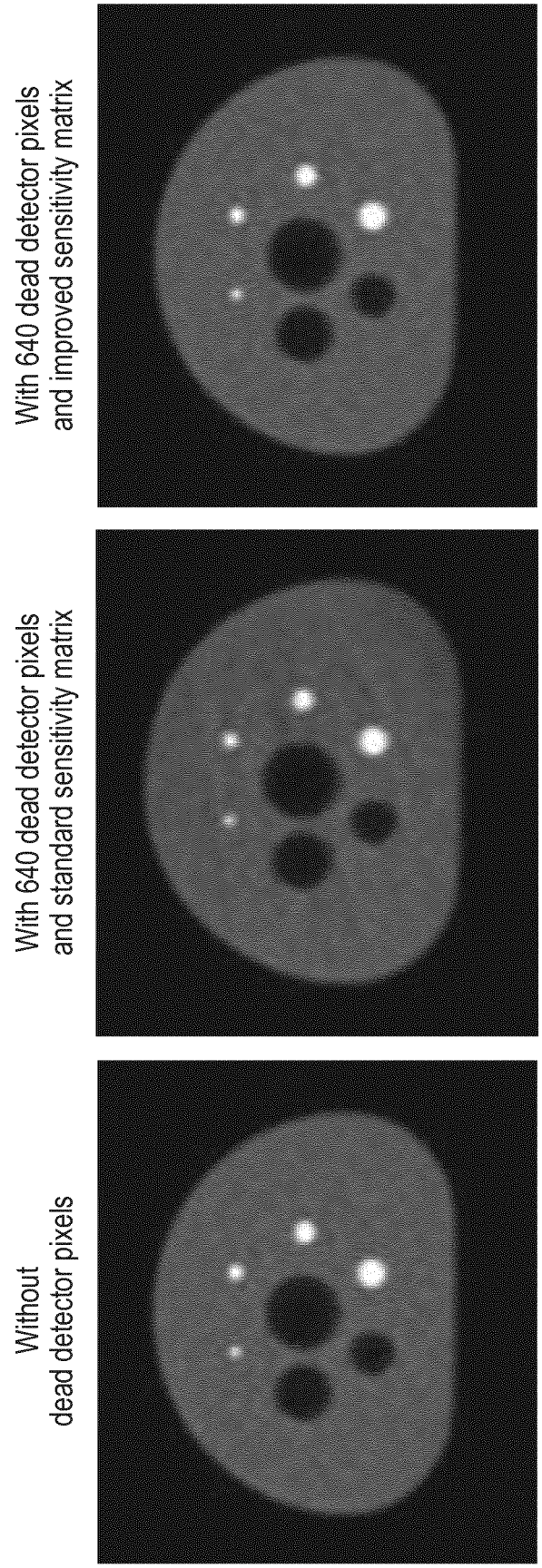

With reference to FIG. 10, an example is shown of the NEMA NU 2 image quality phantom image from iterative list mode reconstruction. The left image is a reference image from data without dead detector pixels. The middle image is with a cluster of 640 dead detector pixels reconstructed using a conventional sensitivity matrix. The righthand image is with the same cluster of 640 dead detector pixels but reconstructed using the improved sensitivity matrix of operation 40.

It will be appreciated that the disclosed approaches may be embodied as a non-transitory storage medium (e.g. one or more hard drives, optical disks, solid state drives or other electronic digital storage devices, various combinations thereof, or so forth) that stores the instructions readable and executable by the computer 10. The non-transitory storage medium may also store the index 32 of dead detector pixels. The non-transitory storage medium may in some embodiments be physically embodied as two or more storage components, e.g. as the combination of a hard disk drive and an optical disk.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A positron emission tomography (PET) imaging device comprising:
    a PET detector array comprising detector pixels configured to acquire counts of oppositely directed 511 keV gamma ray pairs along lines of response (LORs);
    a computer; and
    a non-transitory storage medium storing:
    an index of dead detector pixels;
    instructions readable and executable by the computer to perform operations including:
        reconstructing the counts along the LORs to generate a reconstructed PET image; and
        correcting the reconstructing for missing LORs which are missing due to the dead detector pixels of the PET detector array by:
        estimating counts along the missing LORs by interpolating counts along LORs neighboring the missing LORs by performing a first interpolation pass in which counts along the missing LORs having at least a minimum number of neighboring LORs that are not missing are interpolated using only counts along LORs that are not missing; and
        performing at least one additional interpolation pass in which counts along the missing LORs having less than the minimum number of neighboring LORs that are not missing are interpolated using at least one of counts along LORs that are not missing and/or interpolated counts from a previous interpolation pass.

2. The PET imaging device of claim 1 wherein:
    the counts along each LOR are acquired by two detector pixels intersected by the LOR; and
    the interpolating of the counts along LORs neighboring a missing LOR includes interpolating the counts along all LORs acquired by two detector pixels each of which is either one of the two detector pixels intersected by the missing LOR or immediately adjacent one of the two detector pixels intersected by the missing LOR.

3. The PET imaging device of claim 1 wherein the reconstructing uses at least one sinogram generated from the combination of the counts along the LORs and the estimated counts along the missing LORs.

4. The PET imaging device of claim 1 wherein the estimating of counts along the missing LORs (60) by interpolating counts along LORs neighboring the missing LORs is performed by adjusting sinogram bin values ($c_j$) by a scaling factor ($\tau_j$) estimated to account for the missing LORs.

5. The PET imaging device of claim 1 further comprising:
    a display;
    wherein the instructions stored on the non-transitory storage medium are readable and executable by the computer to perform the further operation of displaying the reconstructed PET image on the display.

6. The PET imaging device of claim 1 wherein:
    the dead detector pixels of the PET detector array are defined as the set of detector pixels which are indexed in the index of dead detector pixels.

7. The PET imaging device of claim 1, further including:
    reconstructing into a reconstructed PET image an image data set including both counts acquired by the PET detector array of oppositely directed 511 keV gamma ray pairs along the LORs and the estimated counts along the missing LORs.

8. The PET imaging device of claim 7, wherein:
    counts along each LOR are acquired by two detector pixels intersected by the LOR; and
    the interpolating of the counts along LORs neighboring a missing LOR includes interpolating the counts along all LORs acquired by two detector pixels each of which is either an operational detector pixel intersected by the missing LOR or immediately adjacent one of the two detector pixels intersected by the missing LOR.

9. The PET imaging device of claim 7, wherein the reconstructing is performed from at least one sinogram generated from the image data set including both the counts acquired by the PET detector array of oppositely directed 511 keV gamma ray pairs along the LORs and the estimated counts along the missing LORs.

10. The PET imaging device of claim 9, further comprising:
computing a sensitivity matrix having matrix elements computed as a summation over all LORs intersecting corresponding image elements excepting the missing LORs;
generating a second reconstructed PET image by performing iterative image reconstruction, using the sensitivity matrix, on a second image data set including the counts acquired by the PET detector array of oppositely directed 511 keV gamma ray pairs along the LORs but not including the estimated counts along the missing LORs; and
generating a reference sinogram by re-projecting (48) the second reconstructed PET image.

11. A non-transitory storage medium storing:
an index of dead detector pixels which identifies dead detector pixels of a positron emission tomography (PET) detector array; and
instructions readable and executable by a computer to generate a reconstructed PET image from counts acquired using the PET detector array of oppositely directed 511 keV gamma ray pairs along lines of response (LORs) by operations including:
computing a sensitivity matrix having matrix elements corresponding to image elements of the reconstructed PET image wherein each matrix element is computed as a summation over all LORs intersecting the corresponding image element excepting missing LORs which are missing due to dead detector pixels indexed in the index of dead detector pixels; and
performing iterative image reconstruction of the counts acquired using the PET detector array to generate the reconstructed PET image wherein the iterative image reconstruction includes normalizing intensities of image elements of the reconstructed PET image using the corresponding matrix elements of the sensitivity matrix.

12. The non-transitory storage medium of claim 11 wherein the computing of the sensitivity matrix comprises computing matrix elements $S_i$ according to:

$$S_i \propto \sum_{j \in \mathcal{D}} H_{ij} \cdot 1$$

where i indexes the image element corresponding to the matrix element $S_i$, j indexes the LORs, $H_{ij}$ is the probability that an electron-positron annihilation initiated at voxel i is detected at LOR j or a projection bin j as a coincidence event, and $\mathcal{D}$ is the set of all LORs intersecting the image element is excepting the missing LORs.

13. The non-transitory storage medium of claim 11 wherein the performing of iterative image reconstruction of the counts comprises performing an iterative maximum likelihood-expectation maximization (MLEM) image reconstruction or an ordered subset expectation maximization (OSEM) reconstruction.

14. The non-transitory storage medium of claim 11 wherein:
the counts acquired using the PET detector array of oppositely directed 511 keV gamma ray pairs along lines of response (LORs) include time-of-flight (TOF) localization; and
the performing of iterative image reconstruction of the counts comprises performing iterative TOF image reconstruction.

15. The non-transitory storage medium of claim 14 further storing:
instructions readable and executable by the computer to display the reconstructed PET image on a display operatively connected with the computer.

* * * * *